US00PP09705P

United States Patent [19]

Austin

[11] Patent Number: Plant 9,705

[45] Date of Patent: Nov. 26, 1996

[54] SHRUB ROSE PLANT NAMED 'AUSMOON'

[75] Inventor: David C. H. Austin, Albrighton, England

[73] Assignee: David Austin Roses Limited, England

[21] Appl. No.: 573,456

[22] Filed: Dec. 15, 1995

[51] Int. Cl.[6] ..... A01H 5/00

[52] U.S. Cl. ..... Plt./1

[58] Field of Search ..... Plt./1, 22

*Primary Examiner*—Howard J. Locker

*Attorney, Agent, or Firm*—Klarquist Sparkman Campbell Leigh & Whinston

[57] ABSTRACT

A repeat flowering, disease resistant shrub rose with old-fashioned shaped flowers, and attractive apricot/yellow coloring.

1 Drawing Sheet

The present invention relates to a new and distinct variety of rose plant of the shrub class which was originated by me by crossing the variety Graham Thomas, unpatented, with the variety Pascali, U.S. Plant Pat. No. 2,592.

The primary objective of this breeding was to produce a new shrub rose variety having repeat flowering and disease resistance, with old-fashioned shaped attractive apricot/yellow flowers. The objective was substantially achieved, along with other desirable improvements, as evidenced by the following unique combination of characteristics that are outstanding in the new variety and that distinguish it from its parents, as well as from all other varieties of which I am aware:

1. Paler yellow, richer apricot flowers than Graham Thomas.
2. Camellia type flatter flowers, fuller than either parent.
3. Bushy habit—less upright than parents.
4. Very good scent—stronger than Graham Thomas.

Asexual reproduction of this new variety by budding, as performed at Albrighton, Wolverhampton, England, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—Graham Thomas.

*Pollen parent.*—(Pascali (U.S. Plant Pat. No. 2,592).

Classification:

*Botanical.*—Rosa Hybrida.

*Commercial.*—Shrub.

FLOWER

Observations made from specimens grown in a garden environment at Albrighton, Wolverhampton, England.

Blooming habit: Recurrent.

Bud:

*Size.*—About 1.5 inches long when the petals start to unfurl.

*Form.*—The bud form is blunt topped, squarish.

*Color.*—When sepals first divide, bud color is Greyed-Purple Group 184A. When half blown, the upper sides of the petals are very pale, almost Yellow Group 4D or 11D but paler; the lower sides of the petals are Yellow Group 4D or Yellow-Orange Group 19D; and base of both sides of petal is deeper Yellow Group 9C.

*Sepals.*—Color: Yellow-Green Group 144B and Greyed-Red Blush Group 180B. Surface texture: Leathery, slightly glandular, slightly hirsute. There are three lightly appendaged sepals. There are two unappendaged sepals with smooth, slightly glandular hairy edges.

*Receptacle.*—Color: Yellow-Green Group 144B and Greyed-Red Group blush 180B. Shape: Funnel, cup. Size: Medium, broad, about 0.4 inches×0.4 inches. Surface: Finely hairy.

*Peduncle.*—Length: Medium, averaging about 1.5 inches. Surface: Finely hirsute, slightly glandular. Color: Light green, bronzy. Strength: Slightly bending.

Bloom:

*Size.*—Medium. Average open diameter is 3.5 inches.

*Borne.*—Several together in clusters of irregular shape having up to 10 flowers per stem.

*Stems.*—Long to medium, normal. Average length is about 18–24 inches.

*Form.*—When first open: Cupped. Permanence: Bloom flattens, petals curl, outer petals curl back, all somewhat quilled.

*Petalage.*—Number of petals under normal conditions: About 110.

*Color.*—Middle one third of petals: The upper sides of the petals are of Yellow-Orange Group 22C. The reverse sides of the petals are Yellow-Orange Group 23D. The base of each of the petals intensifies to Yellow Group 12B. The major color on the upper side is Yellow-Orange Group 22C. Outer quarter to one third of petals are very pale Yellow Group 4D or 11D, but paler. Inner quarter to one third of petals on upper side are a very deep Yellow-Orange Group 23B, and on reverse side Orange Group 24B/C.

*Variegations.*—None.

*Discoloration.*—The general tonality at the end of the first day: Slightly paler. At the end of the third day: Paler, less orange.

*Fragrance.*—Strong tea rose.

Petals:

*Texture.*—Quite leathery in older flowers, medium thick, silky when young.

*Shape.*—Outer petals: Broad, notched, deltoid, heart-shaped. Inner petals: Narrower, longer heart-shaped, notched.

*Form.*—Edges moderately quilled.

*Arrangement.*—Informal, with a few large petaloids in the center. Inner petals and petaloids caught into calyx.

*Persistence.*—Petals drop off cleanly before drying.

*Lastingness.*—On the plant: Long, about six days. As a cut flower: Fair, about four days.

Reproductive parts:

*Anthers.*—Size: Medium. Quantity: Many. Color: Yellow. Arrangement: Tucked in calyx or partly so, mixed with petaloids.

*Filaments.*—Color: Yellow.

*Pollen.*—Color: Gold yellow.

*Styles.*—Color: Green-White Group 157B, some cerise streaks at top.

*Stigmas.*—Color: Yellow.

Form: Shrub.

Growth: Vigorous, upright, branching, sprawling. Mature plant about three feet in height and three and one half feet in width.

Foliage: Number of leaflets on normal mid-stem leaves: 7.

*Size.*—Large, about 6.5–7.0 inches high×inches wide.

*Quantity.*—Abundant to normal.

*Color.*—New foliage: Yellow-Green Group 148A and Greyed-Purple Group 184A blush. New growth markedly red. Old foliage: Yellow-Green Group 147A.

Leaflets:

*Shape.*—Oval to pointed oval.

*Texture.*—Upper side: Leathery.

*Edge.*—Serrated.

*Serration.*—More or less single, shallow.

*Petiole rachis.*—Color: Reddish.

*Petiole underside.*—Prickles, 0–2 per internode.

*Stipules.*—Medium, serrated, about 0.8 inches.

*Disease resistance.*—Resistant to mildew and black-spot under normal growing conditions at Albrighton, Wolverhampton, England.

Wood:

*New wood.*—Color: Reddish (very red Greyed-Purple Group 184A). Bark: Smooth.

*Old wood.*—Color: Very reddish, eventually turning green. Bark: Smooth.

Prickles:

*Quantity.*—On main canes from base: Ordinary. On laterals from main canes: Ordinary.

*Form.*—Long to medium, hooked downward.

*Color when young.*—Red.

*Position.*—Evenly distributed around stem.

Small prickles:

*Quantity.*—On main stalks: None. On laterals: None.

I claim:

1. A new and distinct variety of rose plant of the shrub class, substantially as herein shown and described, characterized particularly as to novelty by the unique combination of its flower petals having a pale yellow, rich apricot color; flat, full old-fashioned shaped flowers; bushy habit; and very good scent.

* * * * *

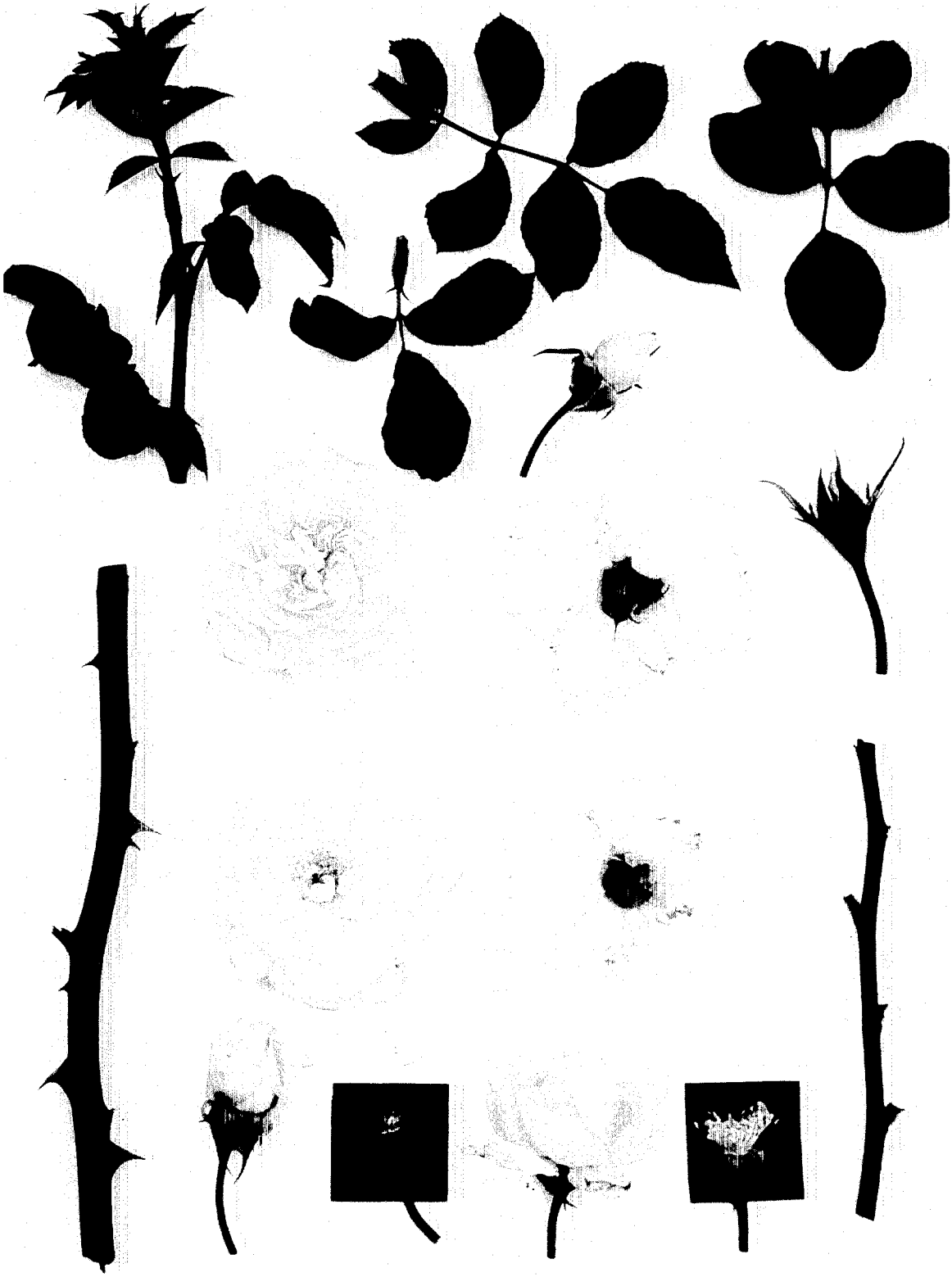

UNITED STATES PATENT AND TRADEMARK OFFICE

CERTIFICATE OF CORRECTION

PATENT NO. : PP9705

DATED : November 26, 1996

INVENTOR(S) : David C. H. Austin

It is certified that error appears in the above-identified patent and that said Letters Patent is hereby corrected as shown below:

Column 3, line 22, "highxinches wide" should read --high X 5 inches wide--.

Signed and Sealed this

Second Day of September, 1997

*Attest:*

*Attesting Officer*

BRUCE LEHMAN

*Commissioner of Patents and Trademarks*